United States Patent
Takahashi et al.

(10) Patent No.: US 8,542,357 B2
(45) Date of Patent: Sep. 24, 2013

(54) METHOD AND DEVICE FOR MEASURING CIRCULAR DICHROISM SPECTRA

(75) Inventors: Hiromi Takahashi, Koganei (JP); Reiko Kuroda, Tokyo (JP); Takunori Harada, Tokyo (JP)

(73) Assignee: The University of Tokyo, Tokyo (JP)

( * ) Notice: Subject to any disclaimer, the term of this patent is extended or adjusted under 35 U.S.C. 154(b) by 325 days.

(21) Appl. No.: 12/935,853

(22) PCT Filed: Apr. 3, 2009

(86) PCT No.: PCT/JP2009/056950
§ 371 (c)(1),
(2), (4) Date: Nov. 3, 2010

(87) PCT Pub. No.: WO2009/123307
PCT Pub. Date: Oct. 8, 2009

(65) Prior Publication Data
US 2011/0063617 A1    Mar. 17, 2011

(30) Foreign Application Priority Data
Apr. 4, 2008    (JP) ................................ 2008-098471

(51) Int. Cl.
*G01J 4/00*    (2006.01)
(52) U.S. Cl.
USPC ........................................................ 356/368
(58) Field of Classification Search
None
See application file for complete search history.

(56) References Cited

U.S. PATENT DOCUMENTS

| | | | |
|---|---|---|---|
| 5,272,354 A | 12/1993 | Kosaka | |
| 6,046,448 A * | 4/2000 | Sato et al. | 356/369 |
| 6,345,115 B1 | 2/2002 | Ramm et al. | |
| 6,480,277 B1 * | 11/2002 | Nafie | 356/364 |
| 2004/0169923 A1 * | 9/2004 | Hug | 359/484 |
| 2005/0094144 A1 * | 5/2005 | Gibbs et al. | 356/365 |
| 2005/0143662 A1 * | 6/2005 | Marchitto et al. | 600/473 |
| 2006/0001876 A1 * | 1/2006 | Gibbs et al. | 356/364 |
| 2009/0009859 A1 * | 1/2009 | Kawai et al. | 356/364 |
| 2009/0033936 A1 | 2/2009 | Otani et al. | |

FOREIGN PATENT DOCUMENTS

| | | |
|---|---|---|
| JP | 49-69381 | 7/1974 |
| JP | 2000-146699 | 5/2000 |
| JP | 2005-321233 | 11/2005 |

OTHER PUBLICATIONS

JP-2000-146699_Detailed Description_—English Machine Translation.*
International Search Report for PCT/JP2009/056950.

* cited by examiner

*Primary Examiner* — Gregory J Toatley
*Assistant Examiner* — Juan D Valentin, II
(74) *Attorney, Agent, or Firm* — Stites & Harbison PLLC; Douglas E. Jackson

(57) ABSTRACT

It is an object of the present invention to solve the above-mentioned problems by using an optical arrangement that is totally different from the conventional CD spectra measuring method, and to provide a method and device for measuring circular dichroism spectra, which can measure the CD spectrum in much shorter time even with the use of a small light source. The method for measuring circular dichroism spectra according to the present invention comprising the steps of irradiating a white light projected from a white light source to a sample without dispersing the light into a monochromatic light, dispersing the light output from the sample, detecting a light intensity of the dispersed light by a detector having a sensor consisting of a charge-coupled device, and then measuring a circular dichroism spectrum of the sample on the basis of a result of the detection by the detector (FIG. 1).

18 Claims, 6 Drawing Sheets

METHOD AND DEVICE FOR MEASURING CIRCULAR DICHROISM SPECTRA

FIELD OF THE INVENTION

This invention relates to an improvement of a method for measuring circular dichroism spectra. Also this invention relates to a device for measuring circular dichroism spectra using said measuring method.

BACKGROUND OF THE ART

The circular dichroism (CD) is the phenomenon that the optical absorption characteristics of the sample to be measured with the right and left circular polarized light are different. CD spectrum is measured to measure the chirality of the optically active material (for example mineral compounds, organic compounds, biological molecules or the like) having chromophore.

In the conventional CD spectra measuring method, a light projected from a light source is dispersed into a monochromatic light by a spectroscope, the monochromatic light is linearly polarized by passing through a light polarizer, the linearly polarized light is circularly polarized by a polarization modulator such as a photoelastic modulator (PEM), and then the circularly polarized light is irradiated to a sample to be measured. The light irradiated to sample is absorbed by the sample according to an optical absorption characteristic thereof. A detector receives the light output from the sample. Then CD spectrum is calculated on the basis of an electric signal corresponding to alight intensity of the light received by the detector.

FIG. 8 is a schematic diagram of the CD spectra-measuring device according to the conventional method for measuring the CD spectra. In the FIG. 8, the numeral number 30 indicates a light source, 31 indicates a spectroscope, 32 indicates a light polarizer, 33 indicates a photoelastic modulator (PEM), 34 indicates a sample cell and 35 indicates a detector.

DISCLOSURE OF THE INVENTION

Problems to be Solved by the Invention

In the above mentioned conventional CD spectra measuring method, at first the light is dispersed into a monochromatic light, and then the monochromatic light is irradiated to the sample. In the conventional method, light quantities decrease significantly to throw away all the light of wavelength except the monochromatic light when the light projected from the light source is dispersed into the monochromatic light so that the light intensity decreases significantly. Therefore, in the conventional method, in order to obtain the light intensity by which the CD spectrum can be finally calculated, the high power source of light of 450 W or more is needed. If such the high power source of light is used, it becomes needing a large-scale cooling system and large-scale the entire measuring device.

Also in the above-mentioned conventional CD spectra-measuring device, in order to obtain the monochromatic light, it is necessary to drive a double prism monochromator, and to scan the wavelength of the light. Therefore there is a problem of requiring time of a few minutes to take a full spectrum so that it is difficult to measure the CD spectrum on a real-time basis.

It is an object of the present invention to solve the above-mentioned problems by using an optical arrangement that is totally different from the conventional CD spectra measuring method, and to provide a method and device for measuring circular dichroism spectra, which can measure the CD spectrum in much shorter time even with the use of a small light source.

Means for Solving the Problems

To achieved the above object, the method for measuring circular dichroism spectra according to the present invention, comprising the steps of irradiating a white light projected from a white light source to a sample without dispersing the light into a monochromatic light, dispersing the light output from the sample, detecting a light intensity of the dispersed light by a detector having a sensor consisting of a charge-coupled device, and then measuring a circular dichroism spectrum of the sample on the basis of a result of the detection by the detector.

Also the device for measuring circular dichroism spectra according to the present invention, a white light source which irradiates a white light, a sample cell in which a sample is disposed, a spectroscope dispersing the light output from the sample cell, and a detector detecting a light intensity of the dispersed light by the spectroscope, which has a sensor consisting of a charge-coupled device, wherein the white light source, the sample cell, the spectroscope, and the detector are disposed on alight path of the white light in series, the white light is irradiated from the white light source to the sample without dispersing the light into a monochromatic light, the light output from the sample is dispersed, the light intensity of the dispersed light is detected by the detector having the sensor consisting of the charge-coupled device, and then a circular dichroism spectrum of the sample is measured on the basis of the light intensity of the dispersed light by the detector.

Advantages of the Invention

The method for measuring circular dichroism spectra according to the present invention, comprising the steps of irradiating a white light projected from a white light source to a sample without dispersing the light into a monochromatic light, dispersing the light output from the sample, detecting a light intensity of the dispersed light by a detector having a sensor consisting of a charge-coupled device, and then measuring a circular dichroism spectrum of the sample on the basis of a result of the detection by the detector. As mentioned above, in the method according to the present invention, since the CD spectrum is measured by using the white light source as the light source without dispersing the light into the monochromatic light, the light is not loss. Therefore, the method according to the present invention becomes possible to measure by using the source of light of an extremely small output, for instance, the source of light of 150 W compared with the conventional measuring method. And the method according to the present invention becomes possible to miniaturize the entire measuring device by using the small light source.

Also in the method according to the present invention since the light projected from the light source is not dispersed into the monochromatic light, time necessary for the measurement can be shortened. With the conventional method, time required for obtaining full spectrum was few minutes. However in the method according to the present invention the detector having the sensor consisting of the charge-coupled device is used, so that it becomes possible to shorten to a few seconds for obtaining full spectrum.

Furthermore, in the present invention sample is disposed on the total reflection boundary surface and the CD spectrum is measured on the basis of the optical absorption by the evanescent light produced when the light is reflected on the total reflection boundary surface. Accordingly, the method according to the present invention can measure any samples without limitation by the state of the sample (for example gaseous state, liquid state and solid state) and can measure the CD spectrum by a high sensitivity with a minute amount of the sample.

The device for measuring circular dichroism spectra according to the present invention, comprising a white light source which irradiates a white light, a sample cell in which a sample is disposed, a spectroscope dispersing the light output from the sample cell, and a detector detecting a light intensity of the dispersed light by the spectroscope, which has a sensor consisting of a charge-coupled device, wherein the white light source, the sample cell, the spectroscope, and the detector are disposed on alight path of the white light in series, the white light is irradiated from the white light source to the sample without dispersing the light into a monochromatic light, the light output from the sample is dispersed, the light intensity of the dispersed light is detected by the detector having the sensor consisting of the charge-coupled device, and then a circular dichroism spectrum of the sample is measured on the basis of the light intensity of the dispersed light by the detector. Accordingly the device according to the present invention has a same effect as one of the above-mentioned method according to the present invention. Especially, the device according to the present invention becomes possible to miniaturize the entire measuring device by the use of a small light source.

THE BEST MODE FOR CARRYING OUT THE INVENTION

The mode for carrying out a method and device for measuring circular dichroism spectra according to the present invention will now be described with reference to some embodiments shown in attached drawings.

FIG. 1 is a schematic diagram of a first embodiment of a device for measuring circular dichroism spectra carrying out a method for measuring circular dichroism spectra according to the present invention.

This device for measuring circular dichroism spectra is a one-time reflection type-measuring device in which a white light is reflected only one-time on a sample in a prism by a total reflection.

In the FIG. 1, the numeral number 1 indicates a white light source of which an output power is about 150 w. The white light projected from the white light source 1 is transmitted to a light polarizer 3 by an optical fiber 2. The white light is linearly polarized at the angle of 45 degrees by the polarizer 3. The linearly polarized light enters into a suitable polarization modulator 4 such as a photoelastic modulator (PEM) or the like and then the light is circularly polarized to the right hand and the left hand. In this embodiment, a modulating frequency of the PEM 4 is 50 kHz.

The white light passing through the PEM 4 is incident into a sample cell 5 that consists of a hemisphere shape prism. A sample 6 is disposed on a total reflection boundary surface of the sample cell 5. The light entered into the sample cell 5 is reflected by a total reflection on the total reflection boundary surface and then the light is exited from the sample cell 5.

The white light exited from the sample cell 5 is received by a detector 9 having a sensor consisting of a charge-coupled device (CCD) through a spectroscope 7 consisting of a small size diffraction grating and a micro-channel plate (MCP) 8. A circular dichroism spectrum (CD spectrum) is calculated on the basis of an electric signal corresponding to a light intensity of the white light received by the detector 9.

A high-speed gate operation of said MCP 8 is synchronized with the modulating frequency of the PEM 4 by a control device not shown in drawings so that the MCP 8 functions as an electronic shutter synchronized with the modulating frequency of the PEM 4.

As mentioned above, in the device for measuring circular dichroism spectra according to the first embodiment of the present invention, the white light source is used as a light source, the white light that is not at all polarized and is not dispersed is circularly polarized, the white light circularly polarized is reflected on the sample 6, and then the white light is dispersed by the small size diffraction grating. Therefore the light loss of this device according to the first embodiment is very low compared with the light loss of the conventional measuring method in which at the beginning the light is dispersed into the monochromatic light by a double prism monochromator having two spectroscopes and being large equipment. Accordingly the size of the measuring device according to the first embodiment may be very small.

Also in this measuring device according to the first embodiment, since the sensor consisting of the charge-coupled device (CCD) is used as the detector 9, it is possible to electrically perform the wavelength scanning so that the scanning speed per one full-spectrum may be very high. Therefore according to the measuring device described above, it is possible to measure the CD spectrum on a real-time basis.

Furthermore, in this measuring device according to the first embodiment, the sample cell 5 consists of the hemisphere prism and after the white light is incident into the sample cell 5, the white light is reflected by the total reflection on the total reflection boundary surface of the prism under the sample 6. Therefore in this measuring device according to the first embodiment the CD spectrum of the sample may be measured on the basis of the optical absorption by an evanescent light produced when the light is reflected on the total reflection boundary surface. Accordingly this measuring device can measure any samples without limitation by the state of the sample (for example gaseous state, liquid state and solid state) and this measuring device can measure the CD spectrum by a high sensitivity with a minute amount of the sample.

Also in this measuring device according to the first embodiment, the spectrum of each wavelength of the light intensity detected by the detector 9 is added in order to reduce the wavelength dependence of the polarization degree of the circular polarized light produced by the PEM 4.

FIG. 2 is a schematic diagram of a second embodiment of the device for measuring circular dichroism spectra carrying out the method for measuring circular dichroism spectra according to the present invention.

This measuring device of the second embodiment is a one-time reflection type-measuring device in which a white light is reflected only one-time on a sample in a prism by a total reflection as well as the measuring device shown in FIG. 1.

In the FIG. 2, the numeral number 11 indicates a white light source of which an output power is about 150 w. The white light projected from the white light source 11 is transmitted to a sample cell 13 by an optical fiber 12. In this second embodiment, sample cell 13 consists of a hemisphere prism and a sample 14 is disposed on a total reflection boundary surface of the sample cell 13. The light, which is incident on the sample cell 13, is reflected by a total reflection on the total reflection boundary surface under the sample 14 and then the light is exited from the sample cell 13.

The white light exited from the sample cell 13 enters into a suitable polarization modulator 15 such as a photoelastic modulator (PEM) or the like and then the white light is circularly polarized to the right hand and the left hand. In this embodiment, a modulating frequency of the PEM 15 is 50 kHz.

The white light exited from the PEM 15 is linearly polarized at the angle of 45 degrees by an analyzer 16. The linearly polarized light passes through a spectroscope 17 and a microchannel plate (MCP) 18. Then said light is received by a detector 19 having a sensor that comprises a charge-coupled device (CCD).

In this embodiment, a high-speed operation of said MCP 18 is synchronized with the modulating frequency of the PEM 15 by a control device not shown drawings so that MCP 18 functions as an electronic shutter synchronized with the modulating frequency of the PEM 15.

Third and forth embodiments of a device for measuring circular dichroism spectra carrying out a method for measuring circular dichroism spectra according to present invention now will be described with reference to FIGS. 3 and 4.

Each of the devices for measuring circular dichroism spectra shown in FIGS. 3 and 4 is a multiple reflection type measuring device in which a white light is reflected more than once in an optical wave-guide.

FIG. 3 is a schematic diagram of the third embodiment of the device for measuring circular dichroism spectra carrying out the method for measuring circular dichroism spectra according to present invention.

This measuring device of the third embodiment has the same structure as one of the first embodiment shown in FIG. 1 excepting that the hemisphere prism is replaced with a slab shape optical wave-guide having a trapezoidal cross section. Therefore, the same numeral numbers as the numeral numbers used in the first embodiment are used for representing same parts as the parts of the first embodiment.

The white light projected from the white light source 1 is transmitted to the polarizer 3 through the optical fiber 2. The white light is linearly polarized by the polarizer 3, and then the linearly polarized light is circularly polarized by the PEM 4.

The circularly polarized white light by the PEM 4 enters into a sample cell 5' consists of the slab shape wave-guide from a light input surface 5a of the sample cell 5'.

The sample 6 is disposed on an upper surface 5b that is a total reflection boundary surface of the sample cell 5'. The white light entered into the sample cell 5' is reflected more than once on the total reflection boundary surface under the sample 6 while the white light is repeatedly reflected by the total reflection in the sample cell 5'. And then the white light exits from the sample cell 5' via a light output surface 5c of the sample cell 5'.

The white light exited from the sample cell 5' is received by the detector 9 having the sensor consisting of the charge-coupled device (CCD) through the spectroscope 7 and the micro-channel plate (MCP) 8. A CD spectrum value is calculated on the basis of an electric signal corresponding to a light intensity of the white light received by the detector 9.

A high-speed gate operation of said MCP 8 is synchronized with the modulating frequency of the PEM 4 by the control device not shown in drawings so that the MCP 8 functions as an electronic shutter synchronized with the modulating frequency of the PEM 4.

As mentioned above, in this third embodiment, since the slab shaped optical wave-guide is used as the sample cell instead of the hemisphere prism, the white light may reflects more than once on the total reflection boundary surface under the sample 6. Therefore, the measuring device of this third embodiment can measure a CD spectrum by a high sensitivity more than the device using the hemisphere prism as the sample sell.

FIG. 4 is a schematic diagram of the fourth embodiment of the device for measuring circular dichroism spectra carrying out the method for measuring circular dichroism spectra according to present invention.

This measuring device of the fourth embodiment has the same structure as one of the second embodiment shown in FIG. 2 excepting that the hemisphere prism is replaced with a slab shape optical wave-guide having a trapezoidal cross section. Therefore, the same numeral numbers as the numeral numbers used in the second embodiment are used for representing same parts as the parts of the second embodiment.

The white light projected from the white light source 11 is transmitted to a sample cell 13' consisting of the slab shape optical wave-guide through the optical fiber 12. The white light is entered into the sample cell 13' via a light input surface 13a of the sample cell 13'.

The sample 14 is disposed on an upper surface 13b that is a total reflection boundary surface of the sample cell 13'. The white light entered into the sample cell 13' is reflected more than once on the total reflection boundary surface under the sample 14 while the white light is repeatedly reflected by the total reflection in the sample cell 13'. And then the white light exits from the sample cell 13' via a light output surface 13c of the sample cell 13'.

The white light projected form the sample cell 13' enters into the suitable polarization modulator 15 such as the photoelastic modulator (PEM) or the like, and then the light is circularly polarized to the right hand and the left hand. In this embodiment, the modulating frequency of the PEM 15 is 50 kHz.

The light projected from the PEM 15 is linearly polarized at the angle of 45 degrees by the analyzer 16, the light linearly polarized passes through the spectroscope 17 and the microchannel plate (MCP) 18, and then the light is received by the detector 19 having the sensor consisting the charge-coupled device (CCD).

The high-speed gate operation of the MCP 18 is synchronized with the module frequency of the PEM 15 by the control device not shown in drawings so that the MCP 18 functions as the electronic shutter synchronized with the modulating frequency of the PEM 15.

Fifth and sixth embodiments of a device for measuring circular dichroism spectra carrying out a method for measuring circular dichroism spectra according to present invention now will be described with reference to FIGS. 5 and 6.

Each of devices for measuring circular dichroism spectra shown in FIGS. 5 and 6 is a transmission type-measuring device in which a white light projected from a light source passes through a sample.

FIG. 5 is a schematic diagram of the fifth embodiment of the device for measuring circular dichroism spectra carrying out the method for measuring circular dichroism spectra according to present invention.

This measuring device of the fifth embodiment has the same structure as one of the first embodiment shown in FIG. 1 excepting the prism as the sample cell is replaced with a transmission type cell. Therefore, the same numeral numbers as the numeral numbers used in the first embodiment are used for representing same parts as the parts of the first embodiment.

The white light projected form the white light source 1 is transmitted to the light polarizer 3 by the optical fiber 2, and then the light is linearly polarized by the polarizer 3. The linearly polarized light is then circularly polarized by the PEM 4.

The white light circularly polarized by the PEM 4 enters into a sample cell 5' consisting of the transmission type cell.

The sample 6 is held in the sample cell 5" so that the white light may pass through the sample 6. The light entered into the sample cell 5" passes through the sample 6 and then exits from the sample cell 5".

The white light exited from the sample cell 5" passes through the spectroscope 7 and the micro-channel plate (MCP) 8, and then the light is received by the detector 9 having the sensor consisting of the charge-coupled device (CCD). A CD spectrum value is calculated on the basis of an electric signal corresponding to a light intensity of the white light received by the detector 9.

A high-speed operation of said MCP 8 is synchronized with the modulating frequency of the PEM 4 by the control device not shown in drawings so that the MCP 8 functions as an electronic shutter synchronized with the modulating frequency of the PEM 4.

FIG. 6 is a schematic diagram of the sixth embodiment of the device for measuring circular dichroism spectra carrying out the method for measuring circular dichroism spectra according to present invention.

This measuring device of the sixth embodiment has the same structure as one of the second embodiment shown in FIG. 2 excepting the prism as the sample cell is replaced with a transmission type cell. Therefore, the same numeral numbers as the numeral numbers used in the second embodiment are used for representing same parts as the parts of the second embodiment.

The white light projected from the white light source 11 is transmitted to a sample cell 13" consisting of the transmission type cell by the optical fiber 12, and then the light enters into the sample cell 13".

The sample 14 is held in the sample cell 13" so that the white light can pass through the sample 14. The light entered into the sample cell 13" passes through the sample 14 and then exits from the sample cell 13".

The white light projected from the sample cell 13' enters into the suitable polarization modulator 15 such as the photoelastic modulator (PEM) or the like and then the white light is circularly polarized to the right hand and the left hand. In this embodiment, the modulating frequency of the PEM 15 is 50 kHz.

The white light exited from the PEM 15 is linearly polarized at the angle of 45 degrees by the analyzer 16. The linearly polarized light passes through the spectroscope 17 and the micro-channel plate (MCP) 18. Then the detector 19 having the sensor consisting of the charge-coupled device (CCD) receives said lights.

In this embodiment, the high-speed operation of said MCP 18 is synchronized with the modulating frequency of the PEM 15 by the control device not shown drawings so that MCP 18 functions as the electronic shutter synchronized with the modulating frequency of the PEM 15.

FIG. 7(*a*) shows a graph where the results of measuring CD spectra of a single-crystal of α-Ni(H$_2$O)$_6$.SeO$_4$ and a single-crystal of α-Ni(H$_2$O)$_6$.SO$_4$ which have a chiral supramolecular arrangement in crystals are shown by using the measuring device according to present invention shown in FIG. 5.

FIG. 7(*b*) shows a graph where the results of measuring the CD spectrums of a single-crystal of α-Ni(H$_2$O)$_6$.SeO$_4$ and a single-crystal of α-Ni(H$_2$O)$_6$.SO$_4$ which have a chiral supramolecular arrangement in crystals are shown by using the conventional measuring device.

In the measuring device according to present invention, a spectrometer SIS-50 made in SYSTEM INSTRUMENTS Co., Ltd. (Japanese company) that uses a polychromator MK-300 made in BUNKOUKEIKI Co., Ltd. (Japanese company) and a ICCD detector made in Andor Technology (United State company) is used as the detector 9. And in the measuring device according to present invention, a white light source of which an output power is 150 w is used as alight source. The voltage of PEM was set to function by 390 nm as ¼ wavelength plate.

The other hand, in the conventional measuring device, a photomultiplier R-376 made in HAMAMATSU PHOTONICS K.K. (Japanese company) is used as detector 35. And a white light source of which an output power is 450 w is used as alight source.

In the conventional measuring method, time required for observation was five minutes as exemplified by the result of a measurement shown in FIG. 7(*b*). However, it took only time for two and a half minutes in the measuring device according to the present invention as exemplified by the result of a measurement shown in FIG. 7(*a*).

In the measurement result shown in FIG. 7(*a*) the CD spectrum is represented by the count that depends on the difference between the light intensity measured with a right hand circular polarization and the light intensity measured with a left hand circular polarization, and the conventional measurement result represents the CD spectrum using elipticity (mdeg). However, it should be appreciated that the CD spectrum shown in FIG. 7(*a*) may be illustrated with values having same order as the conventional one by counting the CD spectrum of FIG. 7(*a*) into, elipticity and then the comparison between the both measurement results may be easily made.

As shown in FIG. 7(*b*), the measuring method and device according to the present invention can measure the CD spectrum even with small-scale source of light compared with the source of light used for the conventional measuring method. Also the measuring method and device according to the present invention can at least reduce the measurement time that is of the necessity in the conventional measuring method by order of magnitudes.

The inventors of the present invention measured the CD spectrum without fine-tuning an optical axis or the like after the measuring device shown in FIG. 5 was set up, and obtained the result of showing in FIG. 7(*a*) in two and a half minutes. Afterwards, the inventors fine-tuned the optical axis or the like, measured the CD spectrum, and were able to obtain the same result as FIG. 7(*a*) in seven seconds.

In the above-mentioned embodiments, the hemi-sphere prism, the optical wave-guide, and the transmission type cell are used for the sample cell, however, without limiting the form of the sample cell to above mentioned embodiments other type cell such as the cylindrical prism or the polygonal prism may be used for the sample cell.

Also the above-mentioned embodiments, the receiving light frequency at the detector is synchronized with the modulating frequency of the PEM by using the micro-channel plate, however, without limiting the method for synchronizing the frequency to above mentioned embodiments, for example a chopper or an external trigger may be used for synchronizing the receiving light frequency at the detector with the modulating frequency of the PEM.

Figure 1:
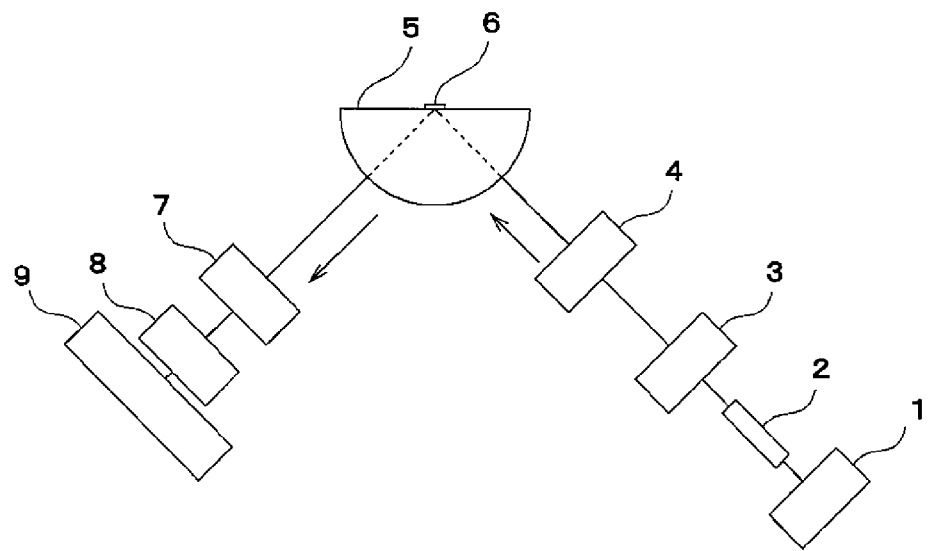
FIG. 1 is a schematic diagram of a first embodiment of a device for measuring circular dichroism spectra carrying out a method for measuring circular dichroism spectra according to the present invention.
Figure 2:
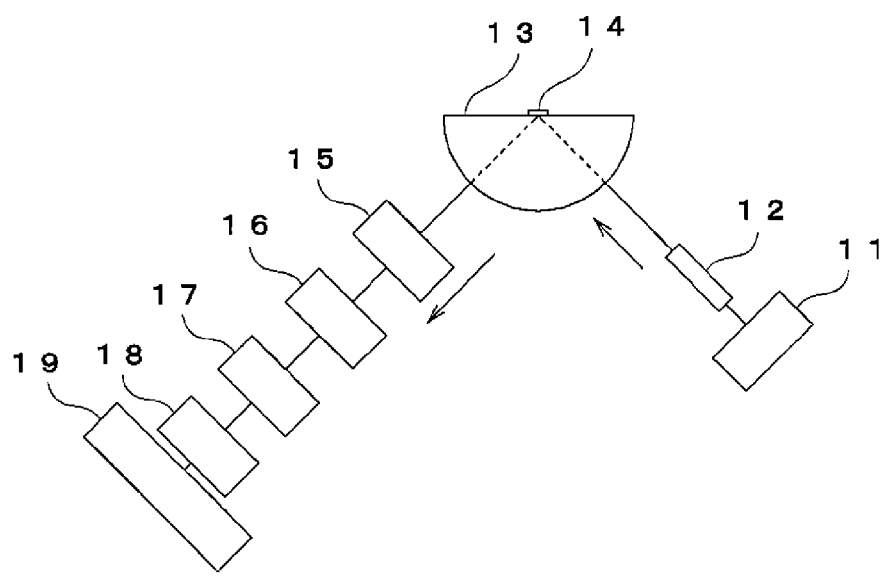
FIG. 2 is a schematic diagram of a second embodiment of the device for measuring circular dichroism spectra carrying out the method for measuring circular dichroism spectra according to the present invention.
Figure 3:
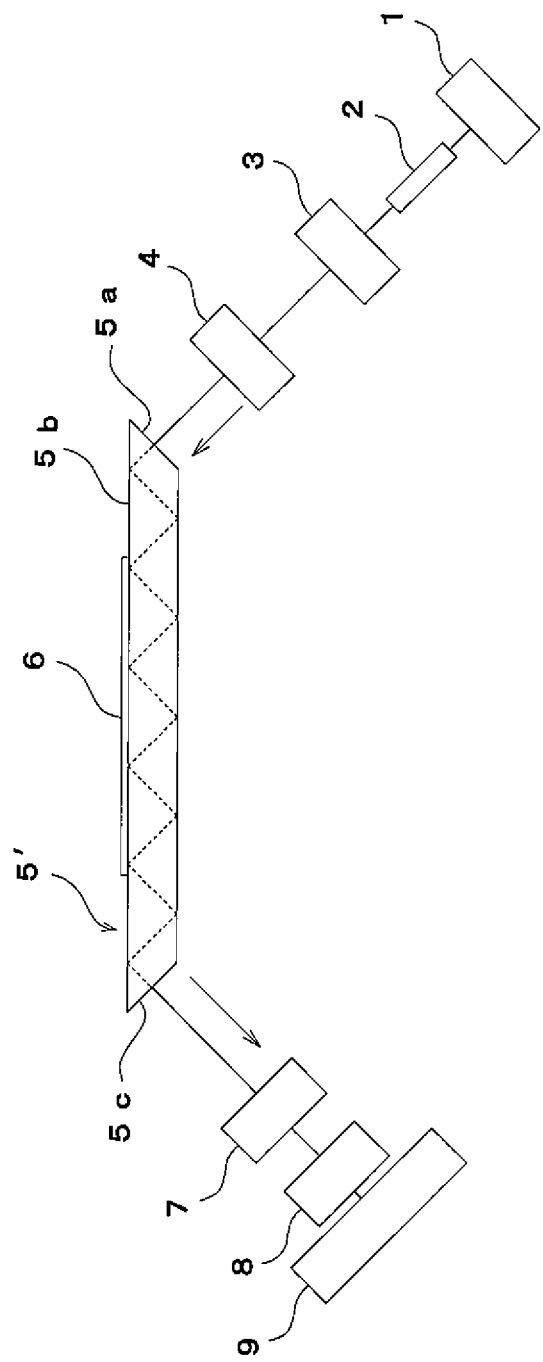
FIG. 3 is a schematic diagram of the third embodiment of the device for measuring circular dichroism spectra carrying out the method for measuring circular dichroism spectra according to present invention.
Figure 4:
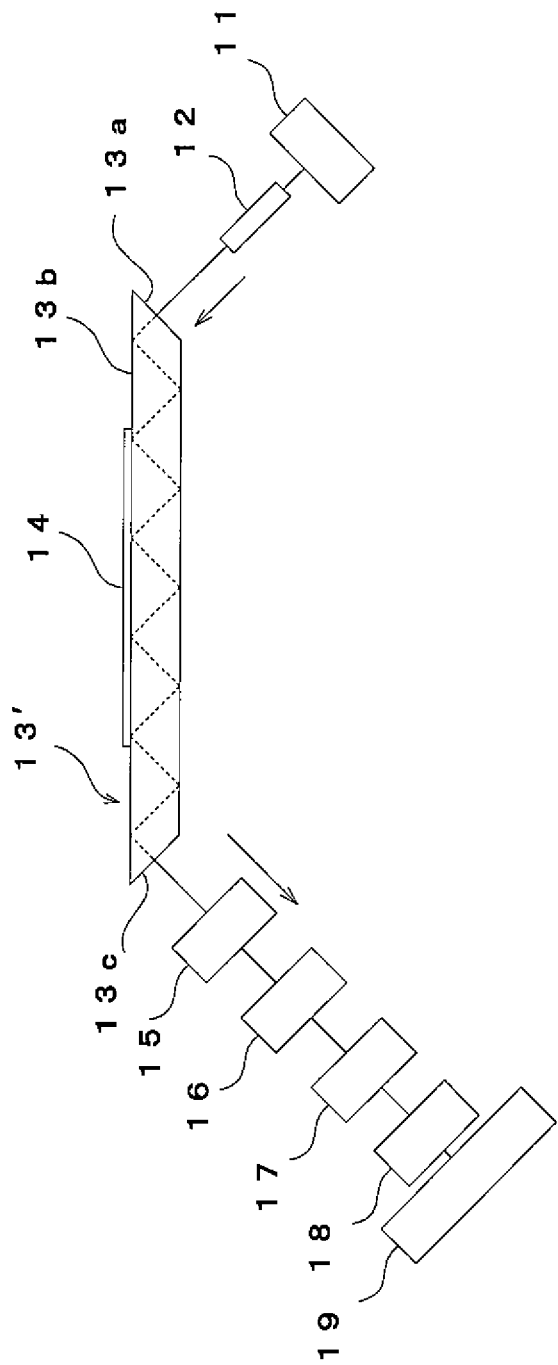
FIG. 4 is a schematic diagram of the fourth embodiment of the device for measuring circular dichroism spectra carrying out the method for measuring circular dichroism spectra according to present invention.
Figure 5:
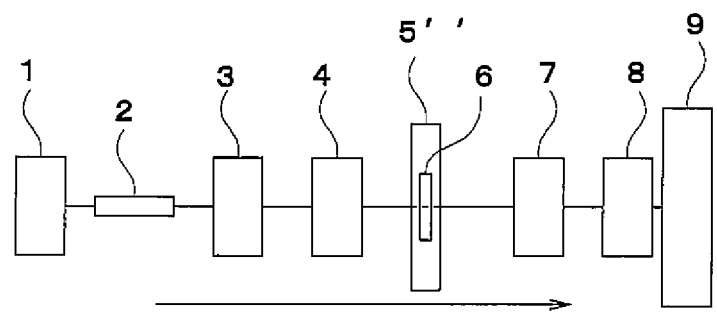
FIG. 5 is a schematic diagram of the fifth embodiment of the device for measuring circular dichroism spectra carrying out the method for measuring circular dichroism spectra according to present invention.
Figure 6:
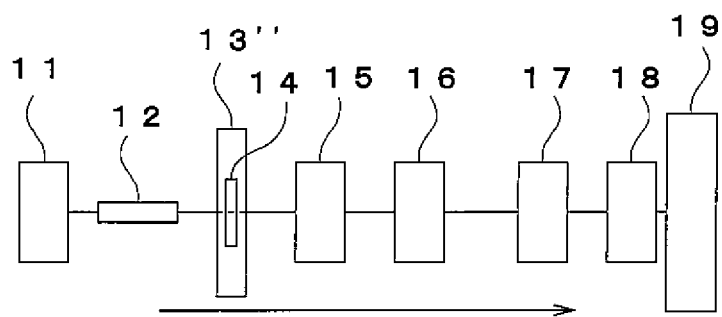
FIG. 6 is a schematic diagram of the sixth embodiment of the device for measuring circular dichroism spectra carrying out the method for measuring circular dichroism spectra according to present invention.
Figure 7:
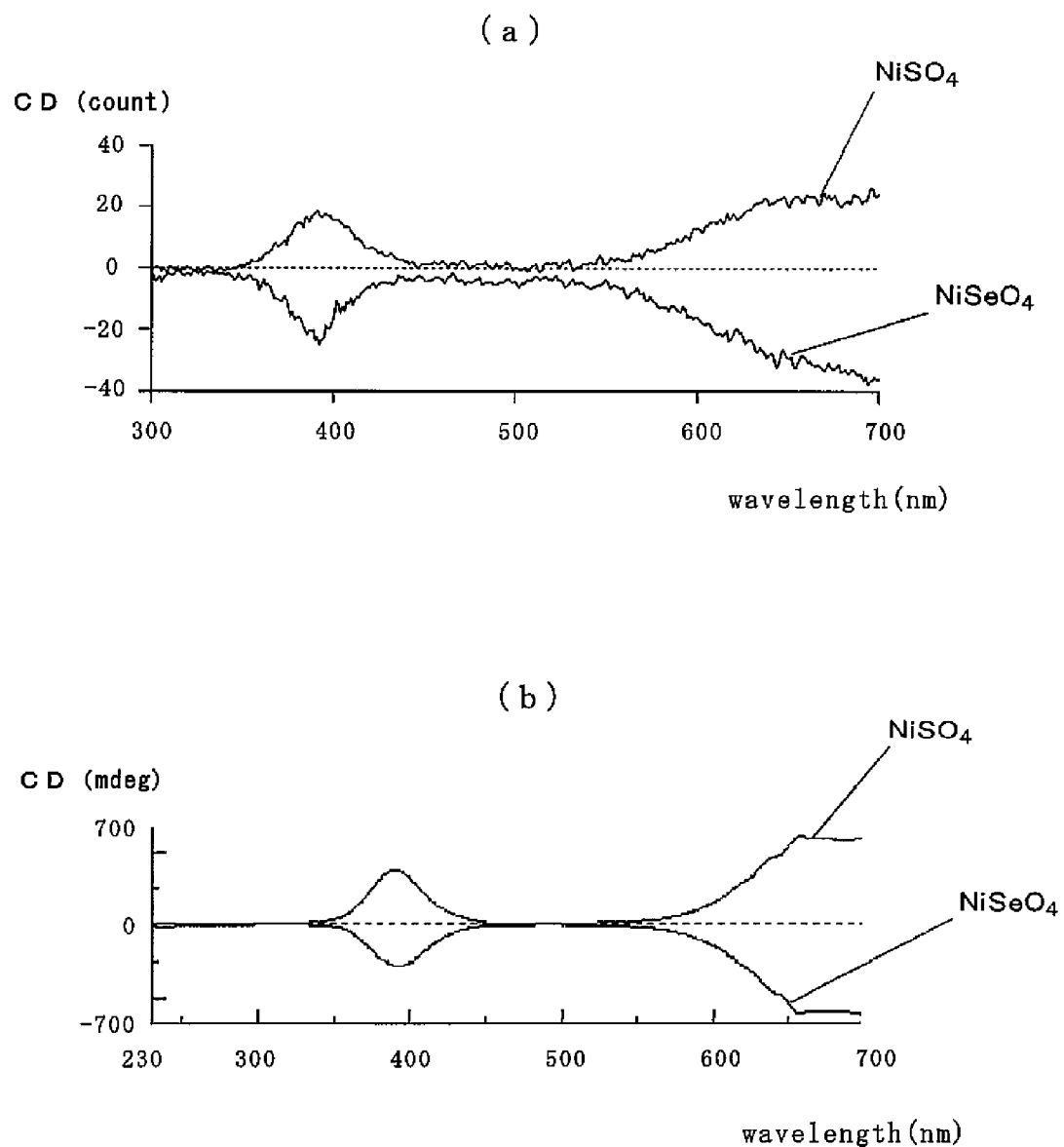
FIG. 7(a) shows a graph where the results of measuring the CD spectrums of a single-crystal of $\alpha$-Ni(H2O)6.SeO4 and a single-crystal of $\alpha$-Ni(H2O)6.SO4 which have a chiral supramolecular arrangement in crystals are shown by using the measuring device according to present invention shown in FIG. 5.
FIG. 7(b) shows a graph where the results of measuring the CD spectrums of a single-crystal of $\alpha$-Ni(H2O)6.SeO4 and a single-crystal of $\alpha$-Ni(H2O)6.SO4 which have a chiral supramolecular arrangement in crystals are shown by using the conventional measuring device.
Figure 8:
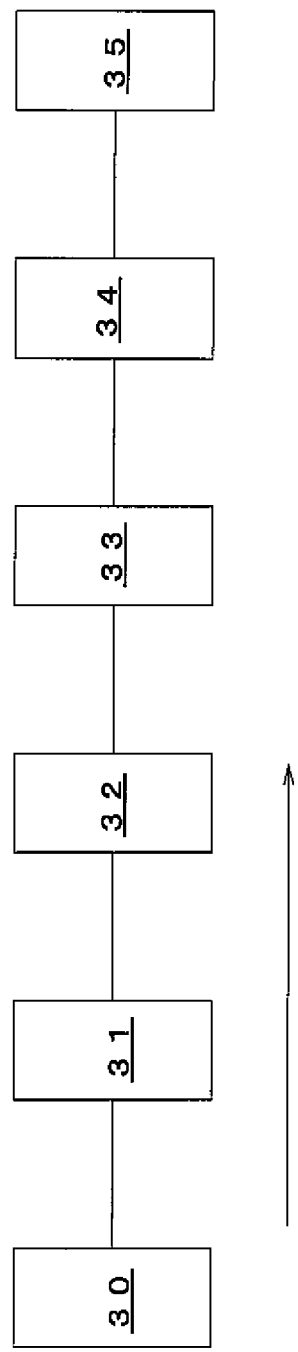
FIG. 8 is a schematic diagram of the CD spectra measuring device according to the conventional method for measuring the CD spectra.

EXPLANATION OF NUMERAL NUMBERS 1 a white light source
2 an optical fiber
3 a light polarizer
4 a polarization modulator
5, 5', 5" a sample cell
5a a light input surface
5b an upper surface
5c a light output surface
6 a sample
7 a spectroscope
8 a micro-channel plate (MCP)
9 a detector
11 a white light source
12 an optical fiber
13, 13', 13" a sample cell
13a a light input surface
13b an upper surface
13c a light output surface
14 a sample
15 a polarization modulator
16 an analyzer
17 a spectroscope
18 a micro-channel plate (MCP)
19 a detector
30 a light source
31 a spectroscope
32 a light polarizer
33 a photoelastic modulator (PEM)
34 a sample cell
35 a detector

The invention claimed is:

1. A method for measuring circular dichroism spectra comprising the steps of:
   irradiating a white light projected from a white light source to a sample without dispersing the light into a monochromatic light,
   dispersing a light output from the sample,
   detecting a light intensity of the dispersed light by a detector having a sensor consisting of a charge-coupled device, and then
   measuring a circular dichroism spectrum of the sample on the basis of a result of the detection by the detector,
   wherein a light input timing into the detector, which detector includes a micro-channel plate, is regulated by the micro-channel plate.

2. The method for measuring circular dichroism spectra according to claim 1, wherein:
   the light projected from the light source is linearly polarized by a light polarizer,
   the linearly polarized light is circularly polarized by a polarization modulator, and then
   the polarized light is irradiated to the sample.

3. The method of measuring circular dichroism spectra according to claim 2, wherein the regulating of the light input timing by the micro-channel plate is on the basis of a modulating frequency of the polarization modulator.

4. The method for measuring circular dichroism spectra according to claim 1, wherein:
   the light output from the sample is circularly polarized by a polarization modulator,
   the circularly polarized light is linearly polarized by a light polarizer, and then the linearly polarized light is dispersed by a spectroscope.

5. The method of measuring circular dichroism spectra according to claim 4, wherein the regulating of the light input timing by the micro-channel plate is on the basis of a modulating frequency of the polarization modulator.

6. The method for measuring circular dichroism spectra according to claim 1, wherein:
   the sample is disposed on a total reflection boundary surface,
   an evanescent light is produced when the light is reflected on the total reflection boundary surface and is used for measuring an optical absorption, and then
   circular dichroism spectrum is measured on the basis of a difference between a right-handed circularly polarized light element and a left-handed circularly polarized light element of the light.

7. The method for measuring circular dichroism spectra according to claim 6, wherein:
   the reflection surface on which the sample is disposed comprises a reflection surface of a sample cell that includes one of an optical wave-guide, a cylindrical shape prism, a hemisphere shape prism or a polygonal shape prism,
   the white light is irradiated to the sample cell, and
   the measuring of the circular dichroism spectrum is performed on the basis of the light that is reflected from the sample on the reflection surface of the sample cell.

8. The method of measuring circular dichroism spectra according to claim 1, wherein:
   a dependence of polarization degree of the circularly polarized light produced by a polarization modulator on a wavelength is reduced by a summation of block spectra on the respective wavelength of the light intensity that is detected by the sensor.

9. A device for measuring circular dichroism spectra comprising:
a white light source which irradiates a white light,
a sample cell in which a sample is disposed,
a spectroscope dispersing the light output from the sample cell, and
a detector detecting a light intensity of the dispersed light by the spectroscope, which has a sensor consisting of a charge-coupled device,
wherein
the white light source, the sample cell, the spectroscope, and the detector are disposed on a light path of the white light in series,
the white light is irradiated from the white light source to the sample without dispersing the light into a monochromatic light,
the light output from the sample is dispersed,
the light intensity of the dispersed light is detected by the detector having the sensor consisting of the charge-coupled device, and then
a circular dichroism spectrum of the sample is measured on the basis of the light intensity of the dispersed light by the detector, and
wherein said detector comprises a micro-channel plate, and
wherein a light input timing into the detector is regulated by the micro-channel plate.

10. The device for measuring circular dichroism spectra according to claim 9, wherein:
a light polarizer and a polarization modulator are disposed in series between the white light source and the sample cell.

11. The device for measuring circular dichroism spectra according to claim 9, wherein:
a light polarizer and a polarization modulator are disposed in series between the sample cell and the spectroscope.

12. The device for measuring circular dichroism spectra according to claim 9, wherein:
said sample cell has a total reflection boundary surface on which said sample is disposed.

13. The device for measuring circular dichroism spectra according to claim 12, wherein:
said sample cell comprises any one of an optical wave-guide, a cylindrical shape prism, a hemisphere shape prism or a polygonal shape prism.

14. A method for measuring circular dichroism spectra comprising the steps of:
irradiating a white light projected from a white light source to a sample without dispersing the light into a monochromatic light,
dispersing the light output from the sample,
polarizing one of the white light or dispersed light both linearly by a light polarizer and circularly by a polarization modulator,
detecting a light intensity of the dispersed light by a detector having a sensor consisting of a charge-coupled device, and then
measuring a circular dichroism spectrum of the sample on the basis of a result of the detection by the detector, and
wherein a dependence of polarization degree of the circularly polarized light on a wavelength is reduced by a summation of block spectra on the respective wavelength of the light intensity that is detected by the sensor.

15. The method for measuring circular dichroism spectra according to claim 14, wherein:
the light projected from the light source is linearly polarized by the light polarizer,
the linearly polarized light is circularly polarized by the polarization modulator, and then
the polarized light is irradiated to the sample.

16. The method for measuring circular dichroism spectra according to claim 14, wherein:
the light output from the sample is circularly polarized by the polarization modulator,
the circularly polarized light is linearly polarized by the light polarizer, and then
the linearly polarized light is dispersed by a spectroscope.

17. The method for measuring circular dichroism spectra according to claim 14, wherein:
the sample is disposed on a total reflection boundary surface,
an evanescent light is produced when the light is reflected on the total reflection boundary surface and is used for measuring an optical absorption, and then
circular dichroism spectrum is measured on the basis of a difference between a right-handed circularly polarized light element and a left-handed circularly polarized light element of the light.

18. The method for measuring circular dichroism spectra according to claim 17, wherein:
the reflection surface on which the sample is disposed comprises a reflection surface of a sample cell that includes one of an optical wave-guide, a cylindrical shape prism, a hemisphere shape prism or a polygonal shape prism,
the white light is irradiated to the sample cell, and
the measuring of the circular dichroism spectrum is performed on the basis of the light that is reflected from the sample on the reflection surface of the sample cell.

* * * * *